US007501531B2

(12) United States Patent
Van Kruchten et al.

(10) Patent No.: US 7,501,531 B2
(45) Date of Patent: Mar. 10, 2009

(54) PROCESS FOR THE PREPARATION OF ALKYLENE CARBONATE

(75) Inventors: Eugene Marie Godfried Andre Van Kruchten, Amsterdam (NL); Hendrik Stichter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 64 days.

(21) Appl. No.: 11/833,129

(22) Filed: Aug. 2, 2007

(65) Prior Publication Data
US 2008/0033185 A1 Feb. 7, 2008

(30) Foreign Application Priority Data
Aug. 3, 2006 (EP) .................. 06254081

(51) Int. Cl.
*C07D 317/36* (2006.01)
*C07D 317/38* (2006.01)

(52) U.S. Cl. .................. 549/230; 549/228; 549/229; 568/858

(58) Field of Classification Search ........... 549/228, 549/229, 230; 568/858
See application file for complete search history.

(56) References Cited

U.S. PATENT DOCUMENTS

| | | | | |
|---|---|---|---|---|
| 2,873,282 | A | 2/1959 | McClellan | 260/340.2 |
| 4,314,945 | A | 2/1982 | McMullen et al. | 260/340.2 |
| 4,786,741 | A | 11/1988 | Sachs | 549/230 |
| 5,218,135 | A | 6/1993 | Buysch et al. | 558/277 |
| 5,391,767 | A | 2/1995 | Mais et al. | 549/229 |
| 6,156,909 | A | 12/2000 | Kim et al. | 549/230 |
| 6,160,130 | A | 12/2000 | Kim et al. | 549/230 |
| 6,399,536 | B2 | 6/2002 | Kim et al. | 502/169 |

FOREIGN PATENT DOCUMENTS

| | | |
|---|---|---|
| EP | 4999924 | 8/1992 |
| JP | 57-106631 | 7/1982 |
| JP | 58-13741 | 1/1984 |

OTHER PUBLICATIONS

J. Palgunadi et al, Ionic Liquid-Derived Zinc Tetrahalide Complexes: Structure and Application to the Coupling Reactions of Alkylene Oxides and $CO_2$, Catalysis Today, vol. 98, 2004, pp. 511-514.
Dae-Won Park et al, "Comparative Studies on the Performance of Immobilized Quaternary Ammonium Salt Catalysts for the Addition of Carbon Dioxide to Glycidyl Methacrylate", Catalysis Today, vol. 98, 2004, pp. 499-504.
H. Kisch et al, "Bifunctional Catalysts for the Synthesis of Cyclic Carbonates from Oxiranes and Carbon Dioxide", Chem. Ber. 119 (1986), pp. 1090-1094. (English language translation provided).
J. Catal (2002) 205, 226-229.
J. Catal (2003) 220, 44-46.
Angew. Chem. Int. Ed (2002) 39 (227), 4096-4098.
Chem. Eur. J. (2003) 9 (3), 678-686.
Chem. Ber. (1986) 119, 1090-1094.
Appl.Catal., A(2005) 228, 48-52.
Appl. Catal., A (2005) 279, 125-129.
Chem. Commun (2006), 1664-1666.
Kirk Othmer's Encyclopedia of Chemical Technology, 4$^{th}$ Edition, vol. 9, 923-940.
J. Polym. Sci, Part A: Polym, Chem, (1993) 31, 939-947.

*Primary Examiner*—Bernard Dentz

(57) ABSTRACT

A process for the preparation of an alkylene carbonate, said process comprising contacting the corresponding alkylene oxide with carbon dioxide in the presence of a metal salt immobilised on a solid support, wherein the metal salt comprises a cation of a metal selected from those in the third period and group 2, the fourth period and groups 2 and 4 to 12, the fifth period and groups 2, 4 to 7, 12 and 14, and the sixth period and groups 2 and 4 to 6 of the periodic table according to IUPAC nomenclature, and an anion selected from anions of inorganic acids and organic acids, and wherein the solid support contains a quaternary ammonium, a quaternary phosphonium, a quaternary arsenonium, a quaternary stibonium, or a ternary sulfonium cation.

20 Claims, No Drawings

PROCESS FOR THE PREPARATION OF ALKYLENE CARBONATE

CROSS-REFERENCE TO RELATED APPLICATIONS

This application claims the benefit of European Patent Application No. 06254081.0, filed Aug. 3, 2006, which is incorporated herein by reference in its entirety.

FIELD OF THE INVENTION

The invention relates to a process for the preparation of alkylene carbonate by the catalytic carboxylation of alkylene oxide.

BACKGROUND OF THE INVENTION

Alkylene carbonates, such as ethylene carbonate and propylene carbonate are widely used as solvents and diluents in industrial processes. They are regularly used as raw materials for commercial products such as cosmetics and pharmaceuticals. Alkylene carbonates can also be used as intermediates in the preparation of alkylene glycols from alkylene oxides.

Alkylene carbonates are produced commercially by the reaction of carbon dioxide with the appropriate alkylene oxide. In the art, ionic halides, such as quaternary ammonium halides, quaternary phosphonium halides and metal halides, are frequently proposed as catalysts for this reaction.

According to JP-A-57,106,631, the preparation of alkylene carbonate as an intermediate in the two-step preparation of alkylene glycol can occur by the reaction of an alkylene oxide with carbon dioxide in the presence of an alkali metal halide.

U.S. Pat. No. 4,314,945 is directed to the preparation of an alkylene carbonate by reaction of the corresponding alkylene oxide with carbon dioxide in the presence of a catalyst characterized by the formula $M^+A^-$, wherein M is potassium and A is iodine or M is a quaternary ammonium cation $(R_1R_2R_3R_4N^+)$ and A is either bromine, chlorine or iodine. The reaction is carried out in alkylene carbonate.

U.S. Pat. No. 4,786,741 is directed to the reaction of alkylene oxide with carbon dioxide in the presence of a catalytic composition and water. Catalytic compositions listed include organic quaternary ammonium halides, organic quaternary phosphonium halides, organic sulphonium halides and organic antimony halides.

JP-A-59,013,741 teaches a method for producing ethylene glycol from ethylene oxide via ethylene carbonate. The reaction of ethylene oxide with carbon dioxide to form ethylene carbonate is catalysed with a quaternary phosphonium halide.

The use of a combination of an alkali metal halide and manganese halide as a catalyst for the preparation of alkylene carbonate from alkylene oxide has been described in U.S. Pat. No. 6,160,130. Lead and indium halides in combination with an alkali metal halide are taught as suitable catalysts for this reaction in U.S. Pat. No. 6,156,909.

Kim et al. have described the use of zinc halides in combination with various other compounds as effective catalysts for the carboxylation of alkylene oxide. In *J. Catal.* (2003) 220, 44-46, catalysts formed by the reaction of 1-alkyl-3-methylimidazolium halides with zinc halides is described. Catalysts comprising zinc halides coordinated with pyridines are described in *Angew. Chem. Int. Ed.* (2000) 39(22), 4096-4098, *Chem. Eur. J.* (2003) 9(3), 678-686 and U.S. Pat. No. 6,399,536.

Mixtures of zinc halides and alkylammonium iodides as catalysts for the conversion of alkylene oxide to alkylene carbonate are taught in *Chem. Ber.* (1986) 119, 1090-1094.

Homogeneous catalysts composed of one of a number of metal salts in combination with a halide selected from the group of alkali metal halides, alkaline earth metal halides, quaternary ammonium, quaternary phosphonium, quaternary arsenonium, quaternary stibonium halides and ternary sulphonium halides have been described for use in the conversion of alkylene oxide to alkylene carbonate in U.S. Pat. No. 5,218,135 and U.S. Pat. No. 5,391,767.

Significant progress has been reported in the development of homogeneous catalysts for the carboxylation of alkylene oxide. However, the use of such catalysts leads to further process steps in order to purify the desired product. Furthermore, as described by Kim et al. in *Appl. Catal., A* (2005) 288, 48-52, separation of alkylene carbonate from homogeneous catalysts by distillation can result in severe decomposition of the alkylene carbonate.

Heterogeneous catalysts for the carboxylation of propylene oxide to propylene carbonate, consisting of quaternary phosphonium halides immobilized on silica, were reported by Takahashi, et al. in *Chem. Commun.* (2006) 1664-1666. The carboxylation of epoxides using catalysts consisting of quaternary ammonium and quaternary phosphonium salts bound to insoluble polystyrene beads was reported by Nishikubo, et al. in *J. Polym. Sci., Part A: Polym. Chem.*, (1993) 31, 939-947.

A solid-supported zinc halide, wherein the solid support is poly(4-vinylpyridine) is described by Kim et al. in *J. Catal.* (2002) 205, 226-229. However, this system is described as having reduced activity in comparison to the equivalent homogeneous system.

A solid-supported system based on zinc halide, wherein the solid support is either poly(4-vinylpyridine) or chitosan is described by Xiao et al. in *Appl. Catal., A* (2005) 279, 125-129. A homogeneous 1-butyl-3-methylimidazolium bromide co-catalyst must also be used in this system.

There still remains a need for a catalyst system for the conversion of alkylene oxides to alkylene carbonates which allows easy purification of the desired product without decomposition of that desired product and still demonstrates high levels of selectivity and activity.

SUMMARY OF THE INVENTION

The present invention provides a process for the preparation of an alkylene carbonate, said process comprising contacting the corresponding alkylene oxide with carbon dioxide in the presence of a metal salt immobilised on a solid support, wherein the metal salt comprises a cation of a metal selected from those in the third period and group 2, the fourth period and groups 2 and 4 to 12, the fifth period and groups 2, 4 to 7, 12 and 14, and the sixth period and groups 2 and 4 to 6 of the periodic table, according to IUPAC nomenclature, and an anion selected from anions of inorganic acids and organic acids, and wherein the solid support contains a quaternary ammonium, a quaternary phosphonium, a quaternary arsenonium, a quaternary stibonium, or a ternary sulfonium cation.

DETAILED DESCRIPTION OF THE INVENTION

We have now surprisingly found that the conversion of alkylene oxides to alkylene carbonates in the presence of carbon dioxide can be efficiently catalysed by a heterogeneous catalytic composition comprising a metal salt on a solid support containing a quaternary ammonium, quaternary phosphonium, quaternary arsenonium, quaternary stibonium or ternary sulfonium cation.

This heterogeneous system allows for facile separation of the desired product from the catalytic composition. Such separation can be accomplished without heating the product in the presence of the catalyst composition at the high temperatures generally required to purify alkylene carbonates by distillation. Further, this heterogeneous catalyst system displays higher levels of activity and selectivity in the conversion of alkylene oxide to alkylene carbonate than the heterogeneous catalyst systems described in the prior art.

The alkylene oxide used as starting material in the process of the invention has its conventional definition, i.e. a compound having a vicinal oxide (epoxy) group in its molecules.

Particularly suitable are alkylene oxides of the general formula (I),

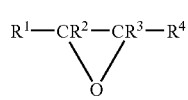

(I)

wherein $R^1$ to $R^4$ independently represent a hydrogen atom or an optionally substituted alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane and 2,3-epoxybutane. In the present invention the most preferred alkylene oxide is ethylene oxide.

Alkylene oxide preparation is well known to the skilled person. In the case of ethylene oxide, it may be prepared by the well known direct oxidation of ethylene, i.e. by air or oxygen oxidation, utilizing silver-based catalysts and often also organic moderators, e.g. organic halides (see for example Kirk Othmer's Encyclopedia of Chemical Technology, 4$^{th}$ edition, Vol. 9, pages 923-940).

As used herein, the term alkylene carbonate refers to a five-membered alkylene carbonate (1,3-dioxolan-2-ones) of the general formula (II),

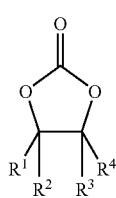

(II)

wherein $R^1$ to $R^4$ correspond to $R^1$ to $R^4$ of the parent alkylene oxide. Therefore suitable alkylene carbonates include ethylene carbonate, propylene carbonate, 1,2-butylene carbonate and 2,3-butylene carbonate. In the present invention the most preferred alkylene carbonate of the general formula (II) is ethylene carbonate, where $R^1$, $R^2$, $R^3$ and $R^4$ all represent hydrogen atoms.

The metal salt used in the process of the present invention comprises a metal cation, wherein the metal is selected from those in the third period and group 2, the fourth period and groups 2 and 4 to 12, the fifth period and groups 2, 4 to 7, 12 and 14, and the sixth period and groups 2 and 4 to 6 of the periodic table according to IUPAC nomenclature (IUPAC Nomenclature of Inorganic Chemistry, Recommendations 1990. Blackwell Scientific Publications, 1990. Edited by G J Leigh); and also an anion selected from anions of inorganic and organic acids.

Preferably, the metal is selected from the group comprising magnesium, calcium, strontium, barium, zinc, copper, manganese, cobalt, nickel, iron, chromium, molybdenum, tungsten, titanium, zirconium, tin, hafnium, vanadium and tantalum, more preferably from the group comprising magnesium, calcium, zinc, cobalt, nickel, manganese, copper and tin. Even more preferably, the metal is selected from the group comprising magnesium, cobalt, copper and zinc. Most preferably, the metal is zinc.

Advantageously, the metal salt anion is selected from the group comprising halides, sulfate, nitrate, phosphate, formate, acetate, propionate, oxalate, butyrate, citrate, succinate, fumarate, maleate, benzoate, phthalate and laurate, preferably from the group comprising halides, acetate, laurate, nitrate and sulphate. More preferably the anion is a halide selected from bromide, iodide and chloride. The most preferable metal salt anions are bromide and iodide.

The solid support of the present invention contains a cationic group selected from quaternary ammonium, quaternary phosphonium, quaternary arsenonium, quaternary stibonium and ternary sulfonium ions. Preferably, the cation is a quaternary ammonium or quaternary phosphonium ion. Most preferably, the cation is a quaternary ammonium ion.

Solid supports suitable for use in the process of the present invention include those of an inorganic nature such as carbon, silica, silica-alumina, zeolites, glass and clays such as hydrotalcite. Such solid supports may have the cation bonded by adsorption, reaction or grafting. Advantageously, in the present invention solid supports comprising a strongly basic ion exchange resin are used, wherein the cation is attached to a polymeric backbone. The polymeric backbone may comprise high molecular weight polymers and co-polymers including polyalkylene, polyester, polycarbonate, polyurethane, formaldehyde resins, etc. Suitable commercially available ion exchange resins include those comprising polyacrylate or styrene-divinylbenzene copolymers as polymeric backbones. Resins with silica-based polymeric backbones, such as polysiloxanes, and resins incorporating vinylpyridine monomers in their polymeric backbones may also be used. Commercially available ion exchange resins suitable for the process of the present invention include, but are not limited to, LEWATIT 500 KR (LEWATIT is a trade mark), AMBERLITE IRA-900, AMBERLITE IRA-458 (AMBERLITE is a trade mark), AMBERJET 4200, AMBERJET 4400 (AMBERJET is a trade mark), DOWEX 1×16 (DOWEX is a trade mark), REILLEX HPQ (REILLEX is a trade mark), MARATHON-A, MARATHON-MSA (MARATHON is a trade mark) and DELOXAN AMP (DELOXAN is a trade mark). Other suitable ion exchange resins include those made according to the method described by Nishikubo, et al. in J. Polym. Sci., Part A: Polym. Chem., (1993) 31, 939-947, which method is hereby incorporated by reference.

Ion exchange resins suitable for use in the process of the present reaction are those in which the anion is a halide, preferably a bromide, iodide or chloride, more preferably a bromide or iodide.

In a preferred embodiment of the present invention, the solid support comprises an ion exchange resin of the general structure:

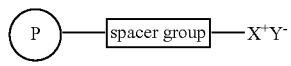

wherein

represents the polymeric backbone of the ion exchange resin, $X^+$ represents the cation of the ion exchange resin, $Y^-$ represents the anion of the ion exchange resin and the spacer group comprises a chemical structure linking the polymeric backbone to the cation. Suitably the spacer group comprises an alkylene group optionally interrupted with one or more oxygen atoms. Therefore, in one embodiment of the present invention, the spacer group is advantageously an unbranched alkylene group of the general formula —$(CH_2)_n$—, wherein n is an integer and is at least 1, preferably at least 2, more preferably at least 3. Suitably, n is at most 10, preferably at most 8, more preferably at most 6. As an illustrative example, LEWATIT 500 KR (LEWATIT is a trade mark), which is based on a divinylbenzene-polystyrene polymeric backbone, has a —$CH_2$— spacer group (i.e. an alkylene group, wherein n is 1). In another embodiment of the invention, the spacer group comprises an alkylene group interrupted with one or more oxygen atoms. In such an embodiment, a preferred spacer group comprises the chemical structure of the general formula —$CH_2$—O—$(CH_2)_n$—, wherein n is an integer in the range of from 1 to 8, preferably in the range of from 1 to 6.

Preferably, the total amount of carbon dioxide supplied to the reactor is an amount of at least 0.5 mol/mol alkylene oxide, preferably at least 1 mol/mol alkylene oxide. Preferably the total amount of carbon dioxide supplied to the reactor is an amount of at most 100 mol/mol alkylene oxide, more preferably in an amount of at most 10 mol/mol alkylene oxide.

The alkylene oxide used in the process of the present invention may comprise purified alkylene oxide or any other suitable alkylene oxide. For example, the alkylene oxide used in the process of the present invention may comprise alkylene oxide from a commercial alkylene oxide plant after it has undergone one or more purification treatments, for example by distillation.

The process of the present invention may be carried out in any suitable solvent known in the art. Preferably the process of the present invention is carried out in a solvent comprising an alkylene carbonate, more preferably said alkylene carbonate comprises the alkylene carbonate which is the intended product of the conversion. For example, the conversion of ethylene oxide to ethylene carbonate may be carried out in an alkylene carbonate such as ethylene carbonate, propylene carbonate or butylene carbonate. Preferably, the conversion of ethylene oxide to ethylene carbonate is carried out in ethylene carbonate.

The process of the present invention may be carried out in the presence of a small amount of water. However, it is preferred to carry out the process of the present invention in the substantial absence of water. An amount of water less than 5000 ppm is suitable; an amount of water of less than 1000 ppm is preferable; an amount of water of less than 100 ppm is most preferable. When using an ion exchange resin as the solid support, it is preferable to subject the ion exchange resin to drying, e.g. vacuum drying, in order to remove water from the ion exchange resin before it is used in the process.

The solid support containing a quaternary ammonium, quaternary phosphonium, quaternary arsenonium, quaternary stibonium or a ternary sulphonium group may be added to the reaction mixture separately from the metal salt. Alternatively, the solid support and metal salt may be pre-mixed before being supplied to the reactor.

Suitably, the molar ratio of the cation on the solid support to the metal salt (based on the metal) in the reaction mixture is in the range of from 20:1 to 1:20, more suitably the molar ratio of the cation to the metal salt (based on the metal) is in the range of from 10:1 to 1:10, most suitably the molar ratio of the cation to the metal salt (based on the metal) is in the range of from 5:1 to 1:5.

Suitably, the metal salt is present in an amount in the range of from 0.0001 to 0.5 mol/mol alkylene oxide (based on the metal). Preferably, the metal salt is present in an amount in the range of from 0.001 to 0.1 mol/mol alkylene oxide (based on the metal).

The process of the present invention can be carried out in any reaction system suitable for a carboxylation process.

The process of the present invention may be carried out in batch operation. However, in particular for large-scale embodiments, it is preferred to operate the process continuously.

Such continuous process can be carried out in fixed bed reactors, operated in up-flow or down-flow. Other reactor options include bubble column reactors and fluidized bed reactors.

The reactors of the present invention may be maintained under isothermal, adiabatic or hybrid conditions. Isothermal reactors are generally shell- and tube reactors, mostly of the multi-tubular type, wherein the tubes contain the catalyst and a coolant passes outside the tubes. Adiabatic reactors are not cooled, and the product stream leaving them may be cooled in a separate heat exchanger.

It may be advantageous for the process of this invention to recycle a part of the reactor output to at least one inlet of the same reactor, because any temperature difference that may arise between the top and the bottom of the reactor is minimised. Accordingly, less external temperature control is required to maintain the reaction temperature than with a conventional reactor. This is particularly advantageous when isothermal conditions are preferred. The part of the reactor output to be recycled may be conveniently separated from the part not to be recycled after the reactor output has left the reactor; or alternatively the part of the reactor output to be recycled may be conveniently removed from the reactor via a different outlet of the reactor than that from which the part of the reactor output not to be recycled is removed. The amount of reactor output mixture to be recycled may be varied to obtain optimum performance with regard to other reaction parameters employed.

In order to accommodate any swelling of the catalyst that may occur during operation, the reactor volume can advantageously be greater than the volume occupied by the catalyst therein, for example in the range of from 10 to 70 vol % greater.

Suitable reaction temperatures for the catalytic carboxylation of alkylene oxides, according to the present invention are generally in the range of from 40 to 200° C.; temperatures in the range of from 50 to 120° C. are preferred.

The reaction pressure is usually selected in the range of from 100 to 5000 kPa, preferably in the range of from 200 to 3000 kPa, most preferably in the range of from 500 to 2000 kPa.

The product alkylene carbonate may find use in any of the applications well known for this class of chemicals. Alternatively, the product alkylene carbonate may be subject to further chemical transformations in order to form other products. In one embodiment of the present invention, the alkylene carbonate that is the product of the process of the present invention is then subjected to a hydrolysis step in order to form the corresponding alkylene glycol.

A problem, which may occasionally arise in certain processes using catalysts containing the above mentioned quaternary or ternary groups, is the presence of small amounts of impurities in the product stream. For example, when strongly basic anion exchange resins, wherein the basic groups comprise quaternary ammonium or phosphonium groups, are used as the solid support for the catalytic group, it has been found that during operation, small amounts of amines or phosphines tend to leach from the resin into the product stream. Other impurities in the product stream may include amines originating from corrosion inhibitors, which may be added to the water used in the process. Although the amounts of such contaminants reaching the end-product are generally very small, they may affect the quality of the end-product such that it may be desirable to reduce the amounts to as low as possible so as not to affect the quality of the product. For example, trimethylamine (TMA) and/or dimethylamine (DMA) may reach the end product in an amount of up to 10 ppm while the fishy odour of TMA may be detected in an amount as low as 1 ppb.

An effective measure in removing such contaminants is the use of a post-reactor bed, containing an acidic species, particularly a strongly acidic ion exchange resin, which effectively captures the contaminants. Strongly acidic ion exchange resins may be of the sulfonic type. Commercially available examples are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S 100 MB and LEWATIT S 100 G1. Such strongly acidic ion exchange resins are available in $H^+$ form and in salt form, such as the $Na^+$ form. When only the $H^+$ form of the strongly acidic resin is used in the post-reactor guard bed, the product stream after passing it may become acidic. Using a mixture of the strongly acidic ion exchange resin in its $H^+$ form and salt form has the advantage of the pH of the product stream remaining close to neutral.

Such a post-reactor bed may be positioned after a carboxylation reaction bed in which the process according to the present reaction is carried out. Alternatively the post-reactor bed may be placed after a subsequent reactor or series of reactors in which the product alkylene carbonate has undergone further chemical transformations, such as hydrolysis to the corresponding glycol. An added advantage of the strongly acidic post-reactor bed positioned after a reactor bed in which the alkylene carbonate has undergone hydrolysis to form the corresponding alkylene glycol is that any remaining alkylene carbonate, which may be still present in the product alkylene glycol product stream, is hydrolysed to alkylene glycol.

In order to allow for exhaustion and replacement or regeneration of the strongly acidic ion exchange resin during operation, it is advantageous to operate the post-reactor bed in two or more separate vessels, to allow the process to be switched between the two vessels, thus maintaining continuous operation.

Exhausted strongly acidic ion exchange resin can be regenerated by treatment with an acid, such as HCl and $H_2SO_4$. Hot sulfuric acid of 0.1 to 2 N has been proven to be effective.

The following Examples will illustrate the invention. Examples 1 to 3 and 30 to 32 are comparative. Examples 4 to 29 and 33 to 36 are of the invention.

EXAMPLES

The following examples were all carried out in a 250 ml Medimex autoclave according to the following procedures.

The LEWATIT, AMBERJET, DOWEX, AMBERLITE and the phosphonium (ex Fluka) resins used in the following examples are all based on a polystyrene/divinylbenzene copolymer backbone. REILLEX HPQ is a resin containing vinylpyridine monomers in which the nitrogen atoms are quaternised. DELOXAN AMP (ex Degussa) is based on a polysiloxane backbone. (LEWATIT, AMBERJET, DOWEX, AMBERLITE, REILLEX and DELOXAN are all trade marks).

Unless otherwise indicated, commercially available strongly basic ion exchange resins were used either in chloride or hydroxide forms. The hydroxide forms were convenient starting materials to prepare ion exchange resins in halide forms, by treatment with hydroiodic acid (HI), hydrobromic acid (HBr) or hydrochloric acid (HCl), according to the following general procedure.

Approximately 40 g of the commercially supplied ion exchange resin (in the OH form) in 100 ml of water was stirred with approximately 15 g of an aqueous HX solution (X=I, Br or Cl; approximately 50%) for 2 hours. The resulting resin was filtered and then washed with water until the wash water was free of HX (i.e. when the wash water had a pH greater than 5).

All ion exchange resin solid supports were dried in a vacuum oven overnight (80° C., 200-250 mm Hg)

General Reaction Conditions A

The reactor was charged with 68 g of propylene carbonate and the metal salt (if present) and ion exchange resin or quaternary ammonium or phosphonium salt (if present) were added in the quantities and ratios shown in Tables 1 and 2. The reactor was then purged with $CO_2$ and pressurized with a $CO_2$ atmosphere of approximately 5 bar (500 kPa). The reactor content was then heated to a temperature of 80° C. and further pressurized with $CO_2$ to 20 bar (2000 kPa). The ethylene oxide was then pumped into the reactor at a rate of 6.3 g/min until a propylene carbonate/ethylene oxide ratio of 0.5 mol/mol was reached. The reactor content was maintained at the above temperature and pressure (by continuous supply of $CO_2$) and samples were taken at regular time intervals and analyzed by GLC. The results are shown in Table 1.

General Reaction Conditions B

After the process according to general reaction conditions type A, the product and solvent were removed by filtration, resulting in a solid catalyst residue composed of the ion exchange resin/metal salt catalyst system. 68 g of propylene carbonate was then added to the reactor. The reactor was then purged with $CO_2$ and pressurized with a $CO_2$ atmosphere of approximately 5 bar (500 kPa). The reactor content was then heated to a temperature of 80° C. and further pressurized with $CO_2$ to 20 bar (2000 kPa). The ethylene oxide was then pumped into the reactor at a rate of 6.3 g/min until a propylene carbonate/ethylene oxide ratio of 0.5 mol/mol was reached. The reactor content was maintained at the above temperature and pressure (by continuous supply of $CO_2$) and samples were taken at regular time intervals and analyzed by GLC.

The results are shown in Table 1.

In order to demonstrate the durability of the catalysts, two catalyst compositions were tested by recycling them for a number of runs. The first run was carried out in accordance with general reaction conditions A, the first recycle run was carried out in accordance with general reaction conditions B and subsequent runs were carried out by subjecting the product from the recycle run to a further recycle run according to general reaction conditions B. The results of these experiments are shown in Table 2.

The catalysts according to the present invention demonstrate excellent selectivity and good activity. Purification of the product ethylene carbonate from the catalyst was carried out by filtration, avoiding the distillation, and resultant decomposition of the product, necessary when using the homogeneous catalysts described in the prior art. The catalysts are robust with little loss in activity and selectivity after recycling.

The importance of the cationic group in the solid support of the present invention is demonstrated by a comparison between Example 3 (comparative, analogous to the prior art system of Kim et al. in *J. Catal.* (2002) 205, 226-229), wherein a resin comprising non-quaternised vinylpyridine monomers is used as the solid support and Example 4 (of the invention) in which a resin comprising vinylpyridine monomers in which the nitrogen atom is quaternised is used as the solid support. The catalytic composition used in Example 4 provides a greatly increased turn-over frequency (TOF) than the catalytic composition used in Example 3, demonstrating higher activity for the catalyst according to the invention. A higher selectivity to ethylene carbonate is also demonstrated by the catalytic composition of the invention (Example 4) over that used in Example 3.

The importance of the metal salt in the process of the present invention is demonstrated by a comparison between Example 31 (comparative), wherein a resin comprising quaternary ammonium cations is used but no metal salt is present and Example 26 (of the invention) in which a resin comprising quaternary ammonium cations is used as the solid support and a zinc halide is present. The process of the invention shows considerably better ethylene oxide (EO) conversion and ethylene carbonate (EC) selectivity. A similar comparison can be made between Example 32 (comparative) and Examples 12, 28 and 29 (of the invention), wherein the processes using a metal salt show better EO conversion. Similar EO conversion and EC selectivity is demonstrated by Example 2 (comparative) and Example 22 (of the invention) even though the quantity of resin used in example 2 was 3.02 g whereas the quantity of resin used in example 22 was 1.16 g.

TABLE 1

| No. | Reaction conditions | Solid support/quaternary salt | | | | Grams metal salt | Cation/metal (mol/mol) | EO conv (1 h) | EC sel (1 h) | TOF (a)* | TOF (b)* |
|---|---|---|---|---|---|---|---|---|---|---|---|
| | | Spacer group | Cation | Anion | Metal salt | | | | | | |
| 1 | A | None | — | — | — | $ZnI_2$ | | — | 2.50 | 80.0 | 3 | 2 |
| 2 | A | AMBERLITE IRA-900 (3.02 g) | $CH_2$ | N | Cl | — | — | — | 2.40 | 99.9 | 0 | 3 |
| 3 | A | PVP† | — | — | — | $ZnBr_2$ | 0.49 | 4.4 | 9.2 | 99.2 | 57 | 9 |
| 4 | A | REILLEX HPQ | — | N | Cl | $ZnBr_2$ | 0.36 | 4.5 | 17.6 | 100 | 150 | 23 |
| 5 | A | Phosphonium (Fluka)# | $(CH_2)_6$ | P | Br | $ZnBr_2$ | 0.17 | 3.7 | 77.9 | 99.8 | 1373 | 240 |
| 6 | A | LEWATIT 500 KR | $CH_2$ | N | Cl | $ZnBr_2$ | 0.58 | 3.6 | 1.50 | 99.6 | 8 | 1 |
| 7 | B | LEWATIT 500 KR | $CH_2$ | N | Cl | $ZnBr_2$ | 0.58 | 3.6 | 15.4 | 99.0 | 80 | 14 |
| 8 | A | LEWATIT 500 KR | $CH_2$ | N | Cl | $ZnI_2$ | 0.84 | 3.6 | 2.80 | 99.9 | 14 | 2 |
| 9 | B | LEWATIT 500 KR | $CH_2$ | N | Cl | $ZnI_2$ | .84 | 3.6 | 14.6 | 99.0 | 75 | 13 |
| 10 | A | LEWATIT 500 KR | $CH_2$ | N | Br | $ZnI_2$ | 0.41 | 3.8 | 3.20 | 99.8 | 25 | 4 |
| 11 | B | LEWATIT 500 KR | $CH_2$ | N | Br | $ZnI_2$ | 0.41 | 3.8 | 31.6 | 100 | 250 | 43 |
| 12 | A | LEWATIT 500 KR | $CH_2$ | N | I | $ZnBr_2$ | 0.22 | 6.6 | 4.50 | 100 | 62 | 7 |
| 13 | B | LEWATIT 500 KR | $CH_2$ | N | I | $ZnBr_2$ | 0.22 | 6.6 | 32.9 | 100 | 457 | 53 |
| 14 | A | AMBERJET 4200 | $CH_2$ | N | Cl | $ZnBr_2$ | 0.18 | 6.4 | 1.70 | 94.0 | 28 | 3 |
| 15 | A | AMBERJET 4200 | $CH_2$ | N | Cl | $ZnBr_2$ | 0.20 | 4.6 | 1.80 | 98.0 | 26 | 6 |
| 16 | A | AMBERJET 4200 | $CH_2$ | N | Cl | $ZnBr_2$ | 0.16 | 6.3 | 1.80 | 99.9 | 103 | 13 |
| 17 | A | AMBERJET 4200 | $CH_2$ | N | Cl | $ZnBr_2$ | 1.02 | 8 | 7.30 | 99.9 | 82 | 8 |
| 18 | A | AMBERJET 4400 | $CH_2$ | N | I | $ZnBr_2$ | 0.29 | 6 | 13.0 | 100 | 137 | 17 |
| 19 | B | AMBERJET 4400 | $CH_2$ | N | I | $ZnBr_2$ | 0.39 | 6 | 21.3 | 100 | 225 | 28 |
| 20 | A | DOWEX 1x16 | $CH_2$ | N | Cl | $ZnI_2$ | 0.63 | 4.3 | 6.00 | 100 | 41 | 7 |
| 21 | A | AMBERLITE IRA-458 | $CH_2$ | N | Cl | $ZnI_2$ | 0.56 | 3.7 | 6.00 | 100 | 47 | 8 |
| 22 | A | AMBERLITE IRA-900 | $CH_2$ | N | Cl | $ZnBr_2$ | 0.21 | 5 | 2.50 | 99.9 | 37 | 5 |
| 23 | A | REILLEX HPQ | — | N | Cl | $ZnBr_2$ | 0.36 | 4.5 | 17.6 | 100 | 150 | 23 |
| 24 | A | DELOXAN AMP | $(CH_2)_3$ | N | Cl | $ZnI_2$ | 0.63 | 4 | 45.4 | 99.2 | 311 | 52 |
| 25 | A | DELOXAN AMP | $(CH_2)_3$ | N | I | $ZnBr_2$ | 0.38 | 3.8 | 6.60 | 99.2 | 53 | 9 |
| 26 | A | Functionalised silica | $(CH_2)_3$ | N | Cl | $ZnBr_2$ | 0.47 | 3.6 | 49.5 | 99.4 | 319 | 57 |
| 27 | B | Functionalised silica | $(CH_2)_3$ | N | Cl | $ZnBr_2$ | 0.47 | 3.6 | 46.3 | 99.4 | 298 | 53 |
| 28 | A | LEWATIT 500 KR | $CH_2$ | N | I | $CoBr_2$ | 0.21 | 6.6 | 3.5 | 75.3 | 37 | 4 |
| 29 | A | LEWATIT 500 KR | $CH_2$ | N | I | $Zn(OAc)_2$ | 0.18 | 6.6 | 5.9 | 97.7 | 80 | 9 |
| 30 | A | — | — | — | — | $Zn(OAc)_2$ | 0.18 | — | 0.4 | 88.7 | 5 | — |

TABLE 1-continued

| | | Solid support/quaternary salt | | | | Grams | Cation/ | EO | | | |
|---|---|---|---|---|---|---|---|---|---|---|---|
| No. | Reaction conditions | Spacer group | Cation | Anion | Metal salt | metal salt | metal (mol/mol) | conv (1 h) | EC sel (1 h) | TOF (a)* | TOF (b)* |
| 31 | A | Functionalised silica | (CH$_2$)$_3$ | N | Cl | — | — | — | 8.6 | 98.6 | 0 | 15 |
| 32 | A | LEWATIT 500 KR | CH$_2$ | N | I | — | — | — | 2.1 | 95.7 | 0 | 4 |

*TOF (a) = mol EC produced per mol catalyst per hour (based on metal, if present);
*TOF (b) = mol EC produced per mol catalyst per hour (based on total halide);
†PVP = polyvinylpyridine weakly basic ion exchange resin, wherein the functional group is not quaternised;
hexyltributylphosphonium bromide on Polystyrene/Divinylbenzene polymer support (ex-Fluka) in bromide form.

TABLE 2

| | | Ion exchange resin | | | | Grams | Cation/ | | | | |
|---|---|---|---|---|---|---|---|---|---|---|---|
| No. | Reaction conditions | | Spacer group | Cation | Anion | Metal salt | metal salt | metal (mol/mol) | EO conv (1 h) | EC sel (1 h) | TOF (a)* | TOF (b)* |
| 5 | A | Phosphonium (Fluka)# | (CH$_2$)$_6$ | P | Br | ZnBr$_2$ | 0.17 | 3.7 | 77.9 | 99.8 | 1373 | 240 |
| 33 | B (first recycle) | Phosphonium (Fluka)# | (CH$_2$)$_6$ | P | Br | ZnBr$_2$ | 0.17 | 3.7 | 65.7 | 99.8 | 1158 | 202 |
| 34 | B (second recycle) | Phosphonium (Fluka)# | (CH$_2$)$_6$ | P | Br | ZnBr$_2$ | 0.17 | 3.7 | 55.5 | 99.8 | 978 | 171 |
| 12 | A | LEWATIT 500 KR | CH$_2$ | N | I | ZnBr$_2$ | 0.22 | 6.6 | 4.5 | 100 | 62 | 7 |
| 13 | B (first recycle) | LEWATIT 500 KR | CH$_2$ | N | I | ZnBr$_2$ | 0.22 | 6.6 | 32.9 | 100 | 457 | 47 |
| 35 | B (second recycle) | LEWATIT 500 KR | CH$_2$ | N | I | ZnBr$_2$ | 0.22 | 6.6 | 22.0 | 100 | 305 | 36 |
| 36 | B (third recycle) | LEWATIT 500 KR | CH$_2$ | N | I | ZnBr$_2$ | 0.22 | 6.6 | 14.2 | 100 | 197 | 23 |

*TOF (a) = mol EC produced per mol catalyst per hour (based on metal);
*TOF (b) = mol EC produced per mol catalyst per hour (based on total halide);
hexyltributylphosphonium bromide on Polystyrene/Divinylbenzene polymer support (ex Fluka).

What is claimed is:

1. A process for the preparation of an alkylene carbonate, said process comprising contacting the corresponding alkylene oxide with carbon dioxide in the presence of a metal salt immobilised on a solid support, wherein the metal salt comprises a cation of a metal selected from the group consisting of metals in the third period and group 2, the fourth period and groups 2 and 4 to 12, the fifth period and groups 2, 4 to 7, 12 and 14, and the sixth period and groups 2 and 4 to 6 of the periodic table according to IUPAC nomenclature, and an anion selected from the group consisting of anions of inorganic acids and organic acids, and wherein the solid support contains a quaternary ammonium, a quaternary phosphonium, a quaternary arsenonium, a quaternary stibonium, or a ternary sulfonium cation.

2. The process as claimed in claim 1, wherein the metal is selected from the group consisting of magnesium, calcium, zinc, cobalt, nickel, manganese, copper, and tin.

3. The process as claimed in claim 1, wherein the anion of the metal salt is selected from the group consisting of halides, acetate, laurate, nitrate, and sulphate.

4. The process as claimed in claim 1, wherein the metal is zinc.

5. The process as claimed in claim 4, wherein the anion of the metal salt is a halide selected from the group consisting of bromide, iodide and chloride.

6. The process as claimed in claim 1, wherein the anion of the metal salt is bromide or iodide.

7. The process as claimed in claim 1, wherein the solid support comprises an ion exchange resin of the general structure:

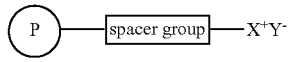

wherein

represents the polymeric backbone of the ion exchange resin, $X^+$ represents the cation of the ion exchange resin, $Y^-$ represents the anion of the ion exchange resin and the spacer group comprises a chemical structure linking the polymeric backbone to the cation of the ion exchange resin.

8. The process as claimed in claim 7, wherein the spacer group comprises a chemical structure of the general formula —(CH$_2$)$_n$—, wherein n is an integer in the range of from 1 to 10.

9. The process as claimed in claim 7, wherein the spacer group comprises a chemical structure of the general formula —CH$_2$—O—(CH$_2$)$_n$—, wherein n is an integer in the range of from 1 to 8.

10. The process as claimed in claim 7, wherein the polymeric backbone of the ion exchange resin comprises a styrene-divinylbenzene copolymer.

11. The process as claimed in claim 7, wherein the polymeric backbone of the ion exchange resin comprises a polyacrylate polymer.

12. The process as claimed in claim 1, wherein the solid support contains a quaternary ammonium cation or a quaternary phosphonium cation.

13. The process as claimed in claim 1, wherein the molar ratio of the cation in the solid support to the metal salt (based on the metal) is in the range of from 20:1 to 1:20.

14. The process as claimed in claim 1, wherein the molar ratio of the cation in the solid support to the metal salt (based on the metal) is in the range of from 5:1 to 1:5.

15. The process as claimed in claim 1, wherein the metal salt is present in an amount in the range of from 0.0001 to 0.5 mol/mol alkylene oxide (based on the metal).

16. The process as claimed in claim 1, wherein the metal salt is present in an amount in the range of from 0.001 to 0.1 mol/mol alkylene oxide (based on the metal).

17. The process as claimed in claim 1, wherein the process is carried out at a temperature in the range of from 40 to 200° C. and at a pressure in the range of from 100 to 5000 kPa.

18. The process as claimed in claim 1, wherein the alkylene oxide is ethylene oxide.

19. A process for the preparation of an ethylene carbonate, said process comprising contacting the corresponding ethylene oxide with carbon dioxide in the presence of a metal salt immobilised on a solid support, wherein the metal salt comprises a zinc halide, and wherein the solid support contains a quaternary ammonium cation.

20. A process for the preparation of alkylene glycol comprising the steps of:
   preparing an alkylene carbonate by a process as claimed in claim 1; and
   hydrolysing the alkylene carbonate.

* * * * *